US007351970B2

(12) United States Patent
Miyao

(10) Patent No.: US 7,351,970 B2
(45) Date of Patent: Apr. 1, 2008

(54) SCANNING ELECTRON MICROSCOPE

(75) Inventor: Hirofumi Miyao, Tokyo (JP)

(73) Assignee: Jeol Ltd., Tokyo (JP)

( * ) Notice: Subject to any disclaimer, the term of this patent is extended or adjusted under 35 U.S.C. 154(b) by 153 days.

(21) Appl. No.: 11/344,804

(22) Filed: Feb. 1, 2006

(65) Prior Publication Data
US 2006/0219911 A1    Oct. 5, 2006

(30) Foreign Application Priority Data
Mar. 8, 2005    (JP) .............................. 2005-063770

(51) Int. Cl.
*H01J 37/244*    (2006.01)
(52) U.S. Cl. ..................................... 250/310
(58) Field of Classification Search ................ 250/310, 250/306
See application file for complete search history.

(56) References Cited

U.S. PATENT DOCUMENTS 6,043,490 A    3/2000    Sakai 6,172,363 B1 *    1/2001    Shinada et al. ............. 250/310

FOREIGN PATENT DOCUMENTS

JP    2003-051435    2/2003

* cited by examiner

*Primary Examiner*—Kiet T Nguyen
(74) *Attorney, Agent, or Firm*—The Webb Law Firm

(57) ABSTRACT

There is disclosed a scanning electron microscope capable of removing the effects of vibrations on image information easily and reliably by detecting variations in the relative position between a specimen chamber holding a specimen therein and the specimen stage. The microscope has an image-processing portion that obtains information about the relative position between the specimen stage and the specimen chamber from a measurement unit when the beam is scanned. Based on the information about the relative position, a pixel position-correcting unit makes corrections to pixel positions indicated by the image information obtained by the scanning. An image creation unit creates image elements to eliminate pixel dropouts or pixel duplication produced by the aforementioned corrections. An image extraction unit extracts an image to be displayed.

11 Claims, 4 Drawing Sheets

SCANNING ELECTRON MICROSCOPE

BACKGROUND OF THE INVENTION

1. Field of the Invention

The present invention relates to a scanning electron microscope for scanning a specimen placed on a specimen stage by an electron beam and obtaining image information about the specimen based on the scanning.

2. Description of Related Art

In recent years, scanning electron microscopes have been used not only in scientific purposes but also for product inspections during various process steps in a manufacturing plant or at the time of shipment. For example, in semiconductor fabrication plants, scanning electron microscopes are used to inspect photolithographically defined silicon wafers. Inspections making use of high magnifications and high resolutions of scanning electron microscopes have become increasingly indispensable.

On the other hand, environments where a scanning electron microscope within a manufacturing plant is installed are different from environments where a scanning electron microscope is installed for scientific purposes. In the former environments, vibrations from the floor surface inevitably enter the instrument. This is undesirable for high-magnification, high-resolution scanning electron microscopes. Furthermore, strengthening of the floor surface and improvement of the installation environments of scanning electron microscopes may involve difficulties because of costs or because the purpose is to inspect finished products incorporated in a production process.

To reduce the effects of vibrations, the rigidity of the scanning electron microscope (especially, the rigidity of the portion located between the specimen stage on which a specimen is placed and the specimen chamber incorporating the stage) has been improved. The specimen is irradiated with an electron beam through the specimen chamber. Thus, variations in the relative position due to vibrations of the electron beam hitting the specimen have been decreased.

In another technique disclosed, for example, in JP 2003-051435 for reducing the effects of vibrations on the image information, vibrations occurring between the specimen stage and specimen chamber are detected. Based on the resulting detection signal, the beam hit position is corrected. In this way, the effects of relative positional variations of the portion located between the specimen stage and the specimen chamber on the image information are reduced.

In a further technique disclosed, for example, in U.S. Pat. No. 6,043,490 for reducing the effects of vibrations on image information, vibrations occurring between the specimen stage and specimen chamber are detected. Based on the resulting detection signal, the obtained image information is processed to reduce the effects of relative positional variations of the portion located between the specimen stage and the specimen chamber on the image information.

However, the effects of variations in the relative position between the specimen stage and the specimen chamber on the image information are not easily removed with any one of the prior art techniques described above. In particular, the scanning electron microscope has a resolution on the order of nanometers. Even if the rigidity of the portion located between the specimen stage and the specimen chamber is improved, it is difficult to remove vibrations comparable to such a resolution. Furthermore, when vibrations of the portion located between the specimen stage and the specimen chamber are detected and the beam hit position is controlled using the resulting detection signal, error is produced due to delay of the control. In addition, in order to detect vibrations occurring between the specimen stage and the specimen chamber and to remove the effects of vibrations on the obtained image information using the detection signal by an image processing technique, it is necessary to perform complex image processing.

It can be seen from the foregoing that it is important how to achieve a scanning electron microscope capable of detecting variations in the relative position between a container having a specimen therein and a specimen stage which is located inside the container and on which the specimen is placed, the microscope being further characterized in that the effects of vibrations on image information can be removed easily and reliably.

SUMMARY OF THE INVENTION

The present invention has been made to solve the foregoing problems with the prior art techniques described above.

It is an object of the present invention to provide a scanning electron microscope which can detect variations in the relative position between a container having a specimen therein and a specimen stage located within the container and carrying the specimen thereon and which can remove the effects of vibrations on image information easily and reliably.

A scanning electron microscope according to a first embodiment of the present invention achieves the above-described object and comprises: a microscope column portion having means for producing an electron beam, focusing the beam onto a specimen, and scanning the beam over the specimen; a stage portion disposed inside a specimen chamber integral with the microscope column portion and having a specimen stage on which the specimen is placed; a detection portion disposed either in the microscope column portion or in the specimen chamber and acting to detect radiation produced from the specimen when the beam is scanned as described above; storage means for storing information about the intensity of the radiation as image information in memory pixel positions corresponding to scan positions on the specimen; measurement means for measuring the relative position between the microscope column portion or the specimen chamber and the specimen stage in synchronism with the scanning; pixel position correction means for making corrections to the pixel positions indicated by the stored image information based on variations in the relative position so as to cancel the variations in the relative position; and image creation means for creating new image information in pixel positions where image information is lost or duplicated by the corrections to the positions.

In this first embodiment, the relative position between the microscope column portion or specimen chamber and the specimen stage is measured in synchronism with the scanning by the measurement means. Thus, information about the relative position is obtained. Corrections are made to the pixel positions indicated by the stored image information by the pixel position correction means to cancel out the variations. The image creation means creates new image information in pixel positions where image information has been lost or duplicated by the corrections to the positions.

A scanning electron microscope according to a second embodiment of the present invention is based on the first embodiment and further characterized in that the stage portion is equipped with a driver portion for moving the specimen stage in a plane substantially perpendicular to the direction of movement of the electron beam.

In this second embodiment, the stage portion moves the specimen stage by the driver portion within the plane substantially perpendicular to the direction of movement of the beam.

A scanning electron microscope according to a third embodiment of the present invention is based on the second embodiment and further characterized in that the measurement means measures the relative position in two mutually perpendicular directions within the plane.

In the third embodiment, the measurement means measures the relative position in the two mutually perpendicular directions within the plane, thus obtaining information about the relative position.

A scanning electron microscope according to a fourth embodiment of the present invention is based on any one of the first through third embodiments and further characterized in that the measurement means is equipped with a laser metrology gauge, linear scale position meter, or capacitance displacement gauge to measure the relative position.

In the fourth embodiment, the measurement means measures the relative position by a laser metrology gauge, linear scale position meter, or capacitance displacement gauge.

A scanning electron microscope according to a fifth embodiment of the present invention is based on any one of the first through fourth embodiments and further characterized in that the measurement means measures the relative position (1) every frame of image which is gained by repeating the scanning in a vertical direction and which provides image information, (2) every line which is gained by repeating the scanning in a horizontal direction and which provides image information, or (3) every line segment which is an integral submultiple of the above-described line and which provides image information.

In the fifth embodiment, the measurement means measures the relative position (1) every frame of image gained by repeating the scanning in a vertical direction, (2) every line which is gained by repeating the scanning in a horizontal direction and which provides image information, or (3) every line segment which is an integral submultiple of the line described previously and which provides image information.

A scanning electron microscope according to a sixth embodiment of the present invention is based on any one of the first through fifth embodiments and further characterized in that the pixel position correction means makes the corrections to the positions (1) every frame of image, (2) every line, or (3) every line segment as described above.

In the sixth embodiment, the pixel position correction means makes the corrections to the positions (1) every frame of image, (2) every line, or (3) every line segment as described above.

A scanning electron microscope according to a seventh embodiment of the present invention is based on any one of the first through sixth embodiments and further characterized in that the image creation means takes the average value of plural sets of image information as new image information at image positions where the plural sets of image information are produced by the corrections to the positions.

In the seventh embodiment, the image creation means takes the average value of plural sets of image information as new image information.

A scanning electron microscope according to an eighth embodiment of the present invention is based on any one of the first through seventh embodiments and further characterized in that the image creation means creates new image information by calculating interpolated values of each dropout pixel position, where image information is lost by the corrections to the positions, from image information at plural pixel positions adjacent to the dropout pixel position or from plural images obtained at successive instants of time at the same pixel position.

In the eighth embodiment, the image creation means takes image information at plural adjacent pixel positions or interpolated values calculated using image information obtained at the same pixel position from plural images obtained at successive instants of time as new information.

As described so far, according to the first embodiment of the present invention, the measurement means measures the relative position between the microscope column portion or specimen chamber and the specimen stage in synchronism with scanning. The pixel position correction means makes corrections to pixel positions indicated by the stored image information, based on variations in the relative position, such that the variations are canceled out. The image creation means creates new image information at pixel positions where image information is lost or duplicated by the corrections to the positions. Therefore, it is possible to gain relative position information precisely corresponding to pixel positions. The effects of vibrations on the image information can be removed easily and reliably, using the relative position information.

According to the second embodiment of the present invention, the stage portion moves the specimen stage within a plane that is substantially perpendicular to the direction of movement of the electron beam by means of the driver portion. Therefore, the beam hit position on the specimen stage can be made optimal for imaging.

According to the third embodiment of the present invention, the measurement means measures the relative position in two directions which are perpendicular to each other within the plane. Therefore, variations in the relative position due to vibrations within the plane can be measured precisely.

According to the fourth embodiment of the present invention, the measurement means measures the relative position by a laser metrology gauge, linear scale position meter, or capacitance displacement gauge. Consequently, the relative position can be measured with high accuracy.

According to the fifth embodiment of the present invention, the measurement means measures the relative position (1) every frame of image which is gained by repeating the scanning in a vertical direction and which provides image information, (2) every line which is gained by repeating the scanning in a horizontal direction and which provides image information, or (3) every line segment which is an integral submultiple of the line and which provides image information. Therefore, data obtained by a measurement can be sampled at optimum intervals according to the period of the vibrations or performance of the measurement means.

According to the sixth embodiment of the present invention, the pixel position correction means makes the corrections to the positions (1) every frame of image, (2) every line, or (3) every line segment as described above. Therefore, the corrections to the pixel positions can be made easily and quickly.

According to the seventh embodiment of the present invention, the image creation means takes the average value of plural sets of image information as new image information and so it is possible to prevent presence of plural sets of image information at one pixel position. In consequence, one set of appropriate image information can be obtained.

According to the eighth embodiment of the present invention, the image creation means creates new image information by calculating interpolated values of each dropout pixel position from image information at plural pixel positions adjacent to the dropout pixel position or from plural images obtained at successive instants of time at the same pixel position. Therefore, any pixel position at which no image information is present can be eliminated. Appropriate image information can be obtained.

Other objects and features of the invention will appear in the course of the description thereof, which follows.

DESCRIPTION OF THE PREFERRED EMBODIMENTS

The preferred embodiments of a scanning electron microscope according to the present invention are hereinafter described with reference to the accompanying drawings. It is to be noted that the invention is not limited thereto.

Figure 1:
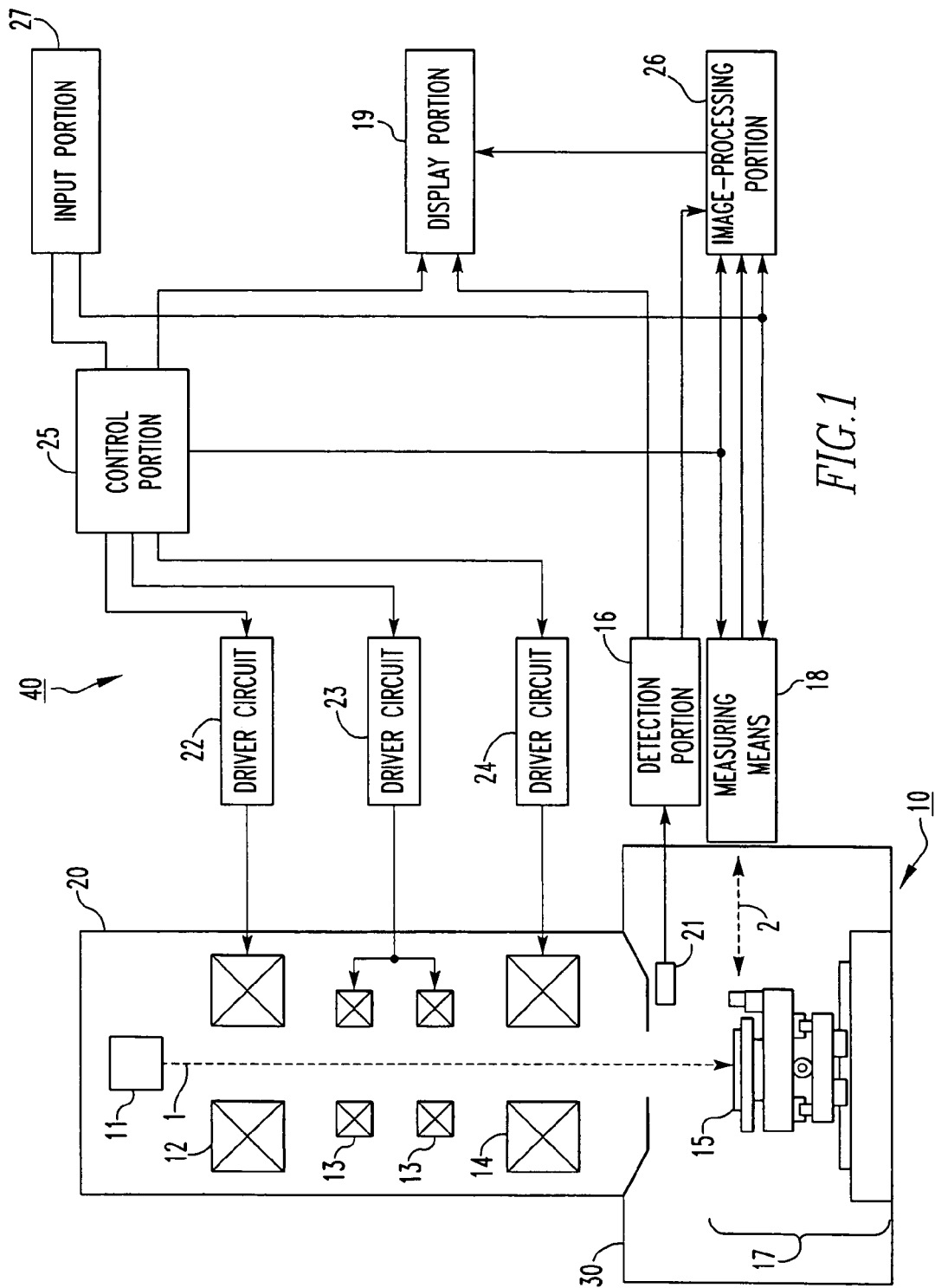
FIG. 1 is a cross-sectional view of a whole scanning electron microscope.

A scanning electron microscope according to an embodiment of the present invention is generally indicated by reference numeral 10 in FIG. 1, which is a cross-sectional view showing the whole structure of the microscope 10. The microscope 10 consists of a microscope column portion 20, a specimen chamber 30, and circuitry 40. The microscope column portion 20 includes an electron gun 11, condenser lenses 12, deflection coils 13, and an objective lens 14. The specimen chamber 30 includes a specimen stage section 17. A specimen 15 is placed inside the chamber 30. The circuitry 40 includes driver circuits 22-24, a control portion 25, a detection portion 16 including sensors 21, an input portion 27, a display portion 19, a measuring means 18, and an image-processing portion 26.

The microscope column portion 20 and specimen chamber 30 form a common vacuum vessel. When imaging is performed, the inside of the vessel is maintained at a vacuum on the order of 10-7 millibar using a pumping system including a rotary pump or molecular pump and an ion pump (none of which are shown). As a result, no residual gas is present inside the vacuum vessel. This prevents scattering of the electron beam 1.

The electron gun 11 accelerates the electrons emitted from the heated filament by the voltage applied between the anode and the gun, thus creating the beam 1 to be directed at the specimen 15. The condenser lenses 12 cooperate with the objective lens 14 to focus the beam 1, which is emitted from the electron gun 11 while spreading, onto the specimen 15.

The deflection coils 13 produce a deflecting magnetic field for scanning the electron beam 1 in both vertical and horizontal directions in two dimensions within the plane perpendicular to the direction of movement. The driver circuits 22-24 produce energizing currents which energize the coils of the condenser lenses 12, deflection coils 13, and objective lens 14 to produce magnetic fields.

The detection portion 16 has the sensors 21 consisting, for example, of semiconductor detectors to detect the intensity of radiation, such as an electron beam emitted from the surface of the specimen 15 irradiated with the electron beam. The electron beam emitted from the specimen surface includes electrons of the beam 1 which have been reflected from the specimen surface, secondary electrons produced from substances at the specimen surface by interaction of the beam 1 with the substances, and Auger electrons produced at the specimen surface. The radiation emitted from the surface of the specimen 15 further includes X-rays or light. Sensors and detection portions adapted for detection of various kinds of radiation are used.

Figure 3:
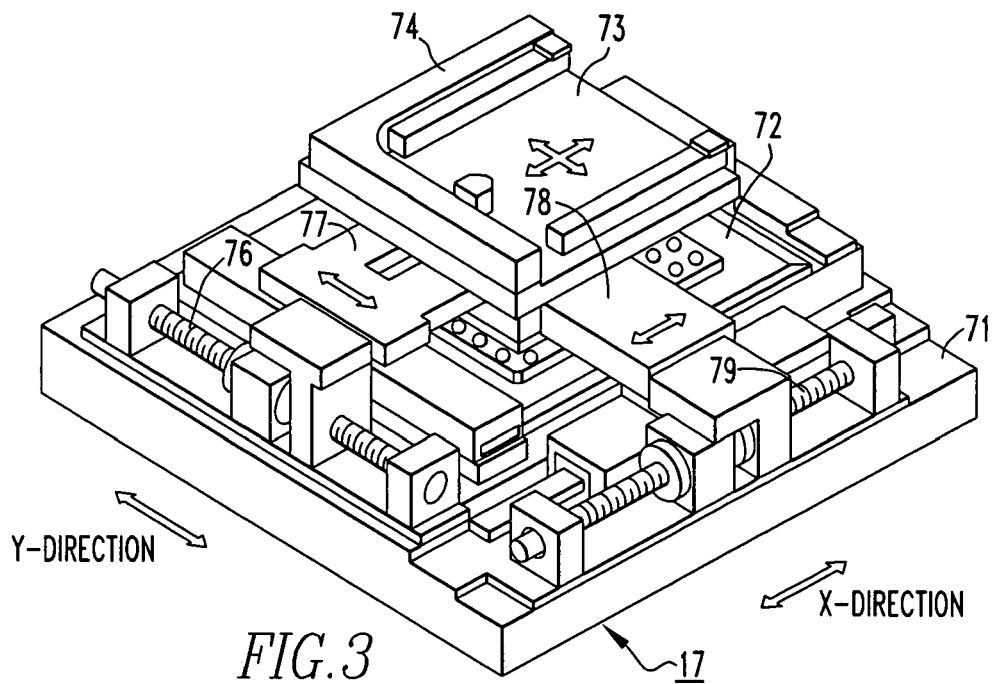
FIG. 3 is a perspective view of a stage portion included in the scanning electron microscope.

The specimen stage section 17 is an XY stage on which the specimen 15, such as a semiconductor wafer, is placed. FIG. 3 is a perspective view showing details of the stage section 17. The stage section 17 includes a specimen stage 73, a mirror 74, a Y-arm 77, a Y-arm driver portion 76, an X-arm 78, an X-arm driver portion 79, a base 72, and a foundation 71. The specimen stage 73 is a stand on which the specimen 15 is placed. The stage 73 is disposed on the base 72 via balls and can move on the base 72 in X- and Y-directions coincident with the horizontal and vertical scanning directions, respectively, of the electron beam 1. An L-shaped mirror 74 is attached to the stage 73. The distance between the stage 73 and the specimen chamber 30 is accurately measured in the X- and Y-directions by a laser metrology gauge (described later). The base 72, Y-arm driver portion 76, and X-arm driver portion 79 are fixed to the foundation 71, which in turn is fixed to the specimen chamber 30.

The X-arm 78 and Y-arm 77 are connected with the X-arm driver portion 79 and Y-arm driver portion 76, respectively, to convert rotary motions of the X-arm driver portion 79 and Y-arm driver portion 76 into translations of the stage 73 in the X- and Y-directions. The arm driver portions 79 and 76 are rotated manually or automatically to bring the stage 73 into an operator's intended position.

Figure 4:
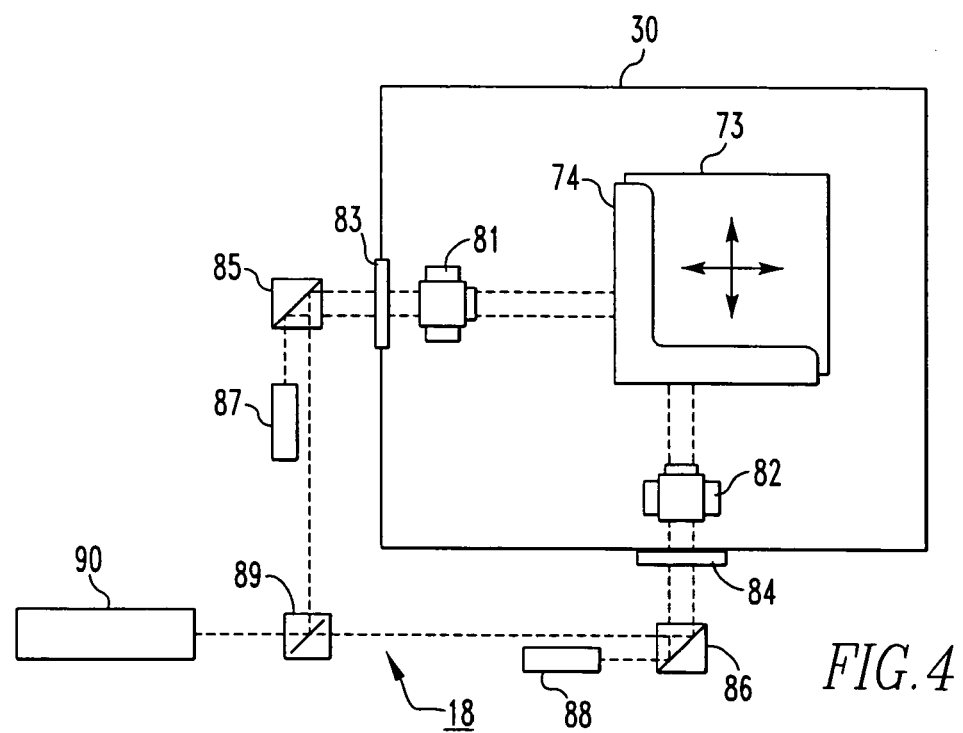
FIG. 4 is a plan view of a measurement means included in the scanning electron microscope.

The measurement means 18 measures the relative position between the specimen stage 73 inside the specimen chamber 30 and the specimen chamber 30 in the X- and Y-directions along which the stage 73 can move. FIG. 4 schematically shows a laser metrology gauge that is an example of the measurement means 18. The laser metrology gauge makes a measurement by directing a laser beam 2 to the mirror 74 via a wall surface of the specimen chamber 30 and measuring light reflected from the mirror 74 by optical interference that provides high measuring accuracy. The measurement means 18 has a laser radiator 90, a beam splitter 89, benders 85, 86 and interferometer units 81, 82. Light-transmitting windows 83 and 84 are present in the wall surfaces of the specimen chamber 30 through which the laser light is transmitted.

The laser radiator 90 emits laser light which is divided into two laser beams traveling in two mutually perpendicular directions by the beam splitter 89. The produced laser beams are reflected in perpendicular directions by the benders 85 and 86 and directed to the mutually perpendicular surfaces of the mirror 74 attached to the specimen stage 73 via the interferometer units 81 and 82. Laser light reflected from the mirror 74 is made to interfere with the incident laser light in the interferometer units 81 and 82, producing interference fringes. The interference fringes are measured by receivers 87 and 88 via the benders 85 and 86. As a result, the relative position between the specimen stage 73 and specimen chamber 30 is measured.

Figure 2:
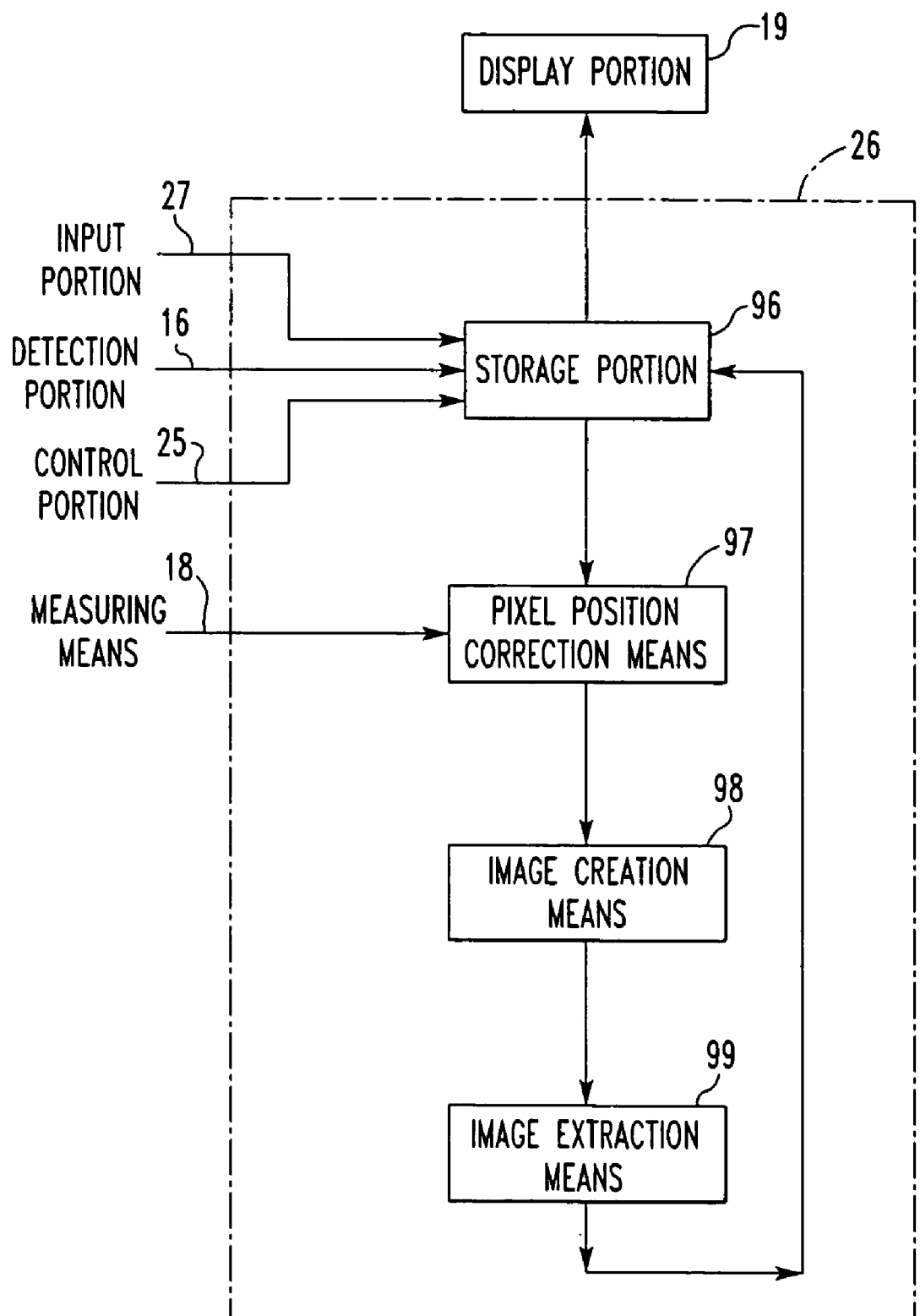
FIG. 2 is a functional block diagram of an image-processing portion included in a scanning electron microscope according to an embodiment of the present invention.

In FIGS. 1 and 2, the input portion 27 consists of an input device, such as a keyboard. Using the input portion, conditions under which imaging is performed by the scanning electron microscope 10 are entered. The input portion also acts as a starting button when image processing is performed by the image-processing portion 26 (described later).

The display portion 19 has a CRT or LCD on which an image of the surface of the specimen 15 is displayed based on analog information that is carried by the electron beam and detected by the detection portion 16.

The control portion 25 controls the electron gun 11, condenser lenses 12, deflection coils 13, objective lens 14, detection portion 16, and display portion 19. The electron beam is focused onto the specimen 15. The beam 1 is scanned over the specimen. The display portion 19 displays an image of the scanned portion of the specimen based on the derived analog information. The control portion 25 sends information about the signals for scanning the electron beam 1, i.e., horizontal and vertical sync signals, to the measurement means 18 and to the image-processing portion 26. The measurement means 18 obtains information about the relative position between the specimen stage 73 and the specimen chamber 30 in the X- and Y-directions in synchronism with the horizontal and vertical sync signals.

The image-processing portion 26 is made of a hardware portion including a calculational portion and a memory. The image-processing portion makes positional corrections to image information, based on information about the intensity of radiation from the detection portion 16 and on information about the relative position between the specimen stage 73 and the specimen, the latter information being derived from the measurement means 18. As a result, the effects of vibrations of the stage 73 on the image information are removed. FIG. 1 is a functional block diagram of the image-processing portion 26, which includes a storage portion 96, a pixel position correction means 97, an image creation means 98, and an image extraction means 99.

The storage portion 96 receives the information about the intensity of radiation from the detection portion 16 and stores the information as digital image information in the memory. The information about the intensity of radiation gained by the detection portion 16 as the analog information is converted into digital information when the information is output from the detection portion 16. The converted digital information is read into the memory in the storage portion 96 in synchronism with the scan sync signal from the control portion 25. The storage portion 96 captures image information and creates image information about the specimen 15. At this time, image information about successive frames of images is stored in the memory.

The pixel position correction means 97 makes corrections to the pixel positions indicated by image information about the specimen 15 stored in the memory by the storage portion 96, based on the information about the relative position between the specimen stage 73 and the specimen chamber, the information being sent from the measurement means 18. Let (Xn, Yn) be the pixel position of a piece of image information n in the memory. Let $\Delta Xn$ and $\Delta Yn$ be a variation in the relative position in the X- and Y-directions, respectively, at this pixel position. Let (Xn', Yn') be a corrected pixel position of the piece of image information in the memory. Thus, we have $$Xn'=Xn-\Delta Xn$$

$$Yn'=Yn-\Delta Yn$$

The components of the variation $\Delta Xn$ and $\Delta Yn$ in the relative position are expressed using positions of pixels or in units common with pixel positions, such as inter-pixel spacing. A negative sign is attached to each component to cancel the variation. This correction to the pixel position indicated by the information about the relative position between the stage 73 and specimen chamber 30 sent from the measurement means 18 is made (1) every frame of image gained by repeated vertical scanning and providing image information, (2) every line gained by repeated horizontal scanning and providing image information, or (3) every line segment that is an integral submultiple of the line described previously and provides image information.

The image creation means 98 corrects either pixel dropouts produced in the image information to which pixel positional corrections have been made or duplication of pixel values and creates new pixel values. After the pixel positions have been corrected using the above equations, the relative position varies by amounts different among frames or lines due to the magnitudes of vibrations. Therefore, pixel positions at which there are no pixel values, i.e., pixel dropouts, occur. Alternatively, line dropouts occur. Also, pixel positions or lines at which pixel values duplicate take place.

If the pixel information suffers from duplication of pixels or lines after corrections to pixel positions, the image creation means 98 supplements the missing pixels or lines by creating new pixels or lines by linear interpolation from the pixel positions or line positions adjacent to the missing pixels or lines. If successive frames of images are stored in the storage portion 96, the image creation means 98 can create new image information by simply averaging image elements produced at the same pixel position over successive frames or performing linear interpolation.

If the pixel information suffers from duplication of pixels or lines after corrections to pixel positions, the image creation means 98 averages the duplicated pixel values at each pixel position where the duplication of pixels or lines has occurred, and takes the obtained average value as new image information at this pixel position. Where image information about successive frames of image is stored in the storage portion 96, the image creation means 98 can accumulate and average image information at the same pixel position across the successive frames of images and take the resulting image as new image information.

The image extraction means 99 extracts that portion of the image information created by the image creation means 98 which is to be displayed and stores the extracted image information into the memory of the storage portion 96. The image extraction means 99 may be placed behind the pixel position correction means 97.

Figure 5:
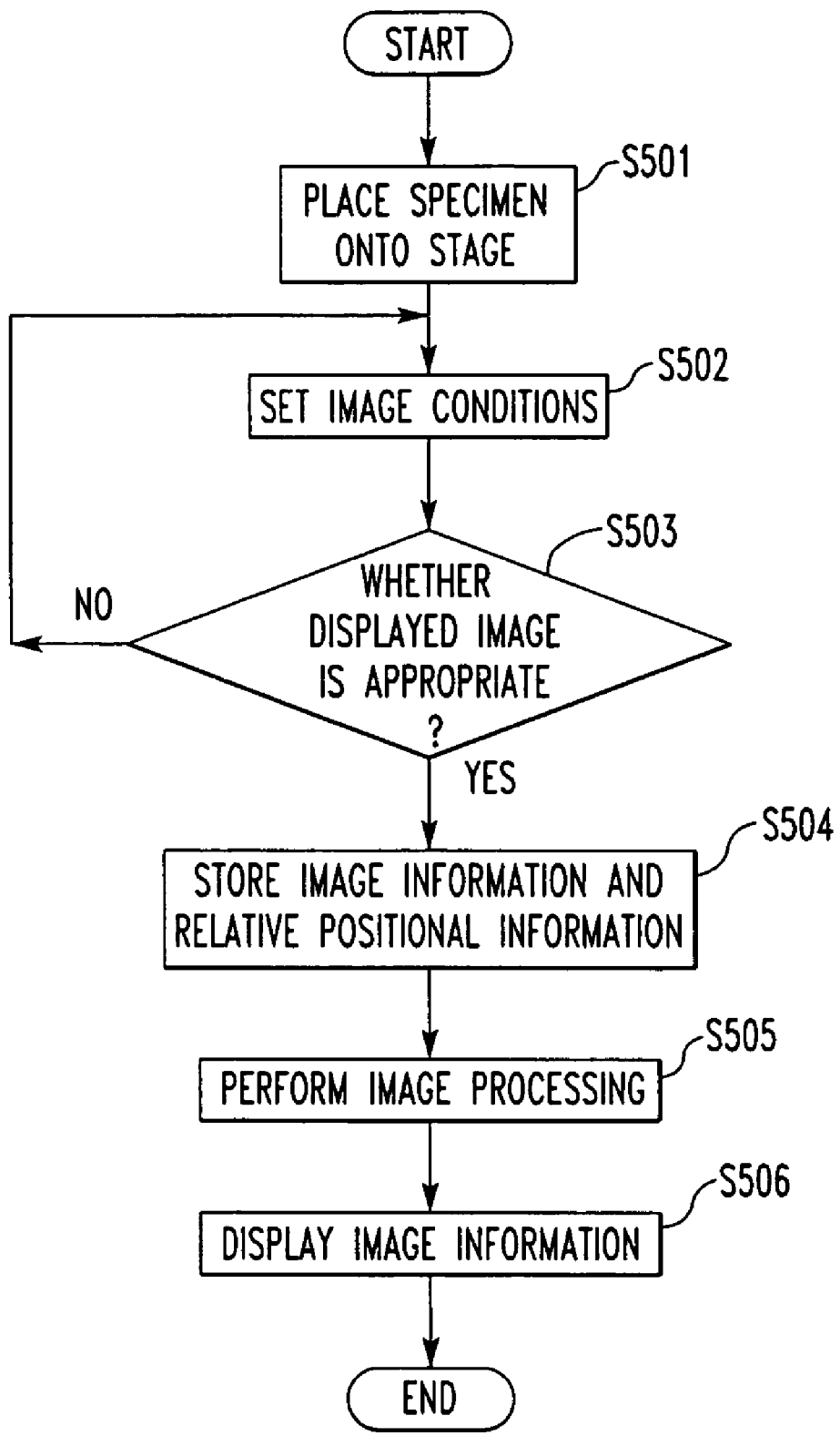
FIG. 5 is a flowchart illustrating a sequence of operations of the scanning electron microscope.

The operation of the scanning electron microscope 10 shown in FIG. 2 is next described. FIG. 5 is a flowchart illustrating a sequence of operations of the microscope 10. First, the operator places the specimen 15, such as a semiconductor wafer, onto the specimen stage 73 (step S501). At this time, if the specimen 15 is a biological material, processing, such as removal of water, is also performed.

The operator then sets imaging conditions from the input portion 27 (step S502). Preparations are made to evacuate the system in which the electron beam 1 travels and to heat the filament of the electron gun 11. Simultaneously with the end of the preparations, the operator sets imaging conditions including the accelerating voltage, the gain of the amplifier (i.e., contrast of the image), probe current, specimen position, and magnification. In consequence, images synchronized to the scanning of the electron beam 1 are displayed real-time on the display portion 19.

Subsequently, the operator makes a decision as to whether the displayed image is in focus (i.e., as to whether the image is appropriate) (step S503). If the image is not appropriate (i.e., the decision of step S503 is negative), control goes to step S502, where the imaging conditions are reset. If the displayed image is appropriate (i.e., the decision of step S503 is affirmative), the operator enters an instruction through the input portion 27 to store the image information in the image-processing portion 26 and to store the relative positional information in the measurement means 18 (step S504). The relative positional information stored in the measurement means 18 pertains to stored image information. This image information is information about the relative position between the specimen stage 73 and the specimen chamber 30 and is obtained by scanning the beam 1.

Then, the image-processing portion 26 gains relative positional information from the measurement means 18 and performs image processing on the stored image information (step S505). During this image processing, pixel positions are corrected by the pixel position correction means 97. Image creation to eliminate pixel dropouts or line dropouts is performed by the image creation means 98. The displayed portion is extracted from the image information by the image extraction means 99. Image information about the extracted display portion is stored in the memory of the storage portion 96.

Thereafter, the processed image information is converted into analog image information and displayed on the display portion 19 or on a display device having a function of displaying digital image information, such as a video monitor (not shown) (step S506). Then, the present processing is ended.

As described so far, in the present embodiment, information about the relative position between the specimen stage 73 and the specimen chamber 30 is gained by the measurement means 18 when the electron beam 1 is scanned. Based on the relative positional information, the image-processing portion 26 makes corrections to pixel positions indicated by the gained image information, creates image elements to eliminate pixel dropouts or duplication of pixels due to the pixel positional corrections, and extracts an image to be displayed. Therefore, during scanning of the electron beam 1, the effects of vibrations of the specimen stage 73 on the image information can be eliminated easily and reliably.

Furthermore, in the present embodiment, the image-processing portion 26 is incorporated within the scanning electron microscope 10. Exactly the same functions as those of the image-processing portion 26 can be imparted to an image-processing system including a personal computer attached to the scanning electron microscope 10 via a communication line.

Additionally, in the present embodiment, the storage portion 96 is incorporated in the image-processing portion 26. Alternatively, the storage means may also be incorporated either in the detection portion 16 or in the control portion 25.

Further, in the present embodiment, a laser metrology gauge is used as an example of the measurement means 18. Alternatively, a linear scale position meter or capacitance displacement gauge may be used.

Having thus described my invention with the detail and particularity required by the Patent Laws, what is desired protected by Letters Patent is set forth in the following claims.

The invention claimed is:

1. A scanning electron microscope comprising:
   a microscope column enclosing means for producing an electron beam, means for focusing the beam onto a specimen, and means for scanning the beam over a specimen;
   a specimen chamber integral with said microscope column portion enclosing a specimen stage on which a specimen may be placed;
   a detector disposed in said microscope column or in said specimen chamber for detecting radiation emitted from a specimen during scanning;
   storage means for storing information about the intensity of the detected radiation as image information in memory pixel positions corresponding to scan positions on the specimen;
   measurement means for measuring a relative position between said specimen stage and said microscope column or said specimen chamber in synchronism with the scanning;
   pixel position correction means for making corrections to the pixel positions indicated by said stored image information based on variations in said relative position so as to cancel said variations; and
   image creation means for creating new image information at pixel positions where image information is lost or duplicated by said corrections to the positions.

2. A scanning electron microscope as set forth in claim 1, wherein said specimen stage portion is equipped with a driver portion for moving said specimen stage in a plane substantially perpendicular to the direction of movement of said electron beam.

3. A scanning electron microscope as set forth in claim 2, wherein said measurement means measures the relative position in two mutually perpendicular directions within said plane.

4. A scanning electron microscope as set forth in claim 2, wherein said measurement means is equipped with a laser metrology gauge, linear scale position meter, or capacitance displacement gauge for measuring said relative position.

5. A scanning electron microscope as set forth in claim 1, wherein said measurement means measures said relative position (a) every frame of image which is gained by repeating said scanning in a vertical direction and which provides image information, (b) every line which is gained by repeating said scanning in a horizontal direction and which provides image information, or (c) every line segment which is an integral submultiple of the above-described line and which provides image information.

6. A scanning electron microscope as set forth in claim 5, wherein said pixel position correction means makes said corrections to the positions (a) every frame of image, (b) every line, or (c) every line segment as described above.

7. A scanning electron microscope as set forth in claim 6, wherein said image creation means creates new image information by calculating interpolated values of each dropout pixel position, where image information is lost by said corrections to the positions, from image information at plural pixel positions adjacent to the dropout pixel position or from plural images obtained at successive instants of time at the same pixel position.

8. A scanning electron microscope as set forth in claim 5, wherein said image creation means creates new image information by calculating interpolated values of each dropout pixel position, where image information is lost by said corrections to the positions, from image information at plural pixel positions adjacent to the dropout pixel position or from plural images obtained at successive instants of time at the same pixel position.

9. A scanning electron microscope as set forth in claim 1, wherein said image creation means takes the average value of plural sets of image information as new image information at image positions where the plural sets of image information are produced by said corrections to the positions.

10. A scanning electron microscope as set forth in claim 9, wherein said image creation means creates new image information by calculating interpolated values of each dropout pixel position, where image information is lost by said corrections to the positions, from image information at plural pixel positions adjacent to the dropout pixel position or from plural images obtained at successive instants of time at the same pixel position.

11. A scanning electron microscope as set forth in claim 1, wherein said image creation means creates new image information by calculating interpolated values of each dropout pixel position, where image information is lost by said corrections to the positions, from image information at plural pixel positions adjacent to the dropout pixel position or from plural images obtained at successive instants of time at the same pixel position.

* * * * *